United States Patent
Miyamoto et al.

(10) Patent No.: US 9,028,510 B2
(45) Date of Patent: May 12, 2015

(54) TISSUE EXCISION METHOD

(71) Applicant: Olympus Medical Systems Corp., Tokyo (JP)

(72) Inventors: Manabu Miyamoto, Tokyo (JP); Takayasu Mikkaichi, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 147 days.

(21) Appl. No.: 13/756,786

(22) Filed: Feb. 1, 2013

(65) Prior Publication Data

US 2014/0222051 A1    Aug. 7, 2014

(51) Int. Cl.

| | |
|---|---|
| A61B 17/3205 | (2006.01) |
| A61B 17/068 | (2006.01) |
| A61B 17/115 | (2006.01) |
| A61B 17/072 | (2006.01) |
| A61B 17/04 | (2006.01) |
| A61B 17/00 | (2006.01) |
| A61B 19/00 | (2006.01) |
| A61B 1/00 | (2006.01) |

(52) U.S. Cl.
CPC ... *A61B 17/3205* (2013.01); *A61B 2017/00269* (2013.01); *A61B 17/07207* (2013.01); *A61B 19/5212* (2013.01); *A61B 2017/00353* (2013.01); *A61B 2017/00818* (2013.01); *A61B 2017/07214* (2013.01); *A61B 2019/521* (2013.01); *A61B 1/00087* (2013.01); *A61B 1/00131* (2013.01)

(58) Field of Classification Search
CPC .............. A61B 17/3205; A61B 17/07207; A61B 2017/00269; A61B 2017/00353; A61B 2017/00818; A61B 2017/07214; A61B 2019/521; A61B 1/00087; A61B 1/00131
USPC ......... 606/139, 140, 153, 157, 106, 110, 144, 606/145, 151; 128/898; 297/175.1; 600/205, 184
See application file for complete search history.

(56) References Cited

U.S. PATENT DOCUMENTS

| | | | |
|---|---|---|---|
| 7,204,821 B1* | 4/2007 | Clare et al. ............... | 604/30 |
| 7,749,235 B2* | 7/2010 | Sheets et al. ............. | 606/139 |
| 2004/0059346 A1* | 3/2004 | Adams et al. ............ | 606/115 |
| 2009/0137984 A1* | 5/2009 | Minnelli ................... | 604/540 |
| 2010/0076417 A1* | 3/2010 | Suckewer et al. ....... | 606/4 |

FOREIGN PATENT DOCUMENTS

| | | |
|---|---|---|
| JP | 8-322787 A | 12/1996 |
| JP | 2004-503325 A | 2/2004 |
| JP | 2007-29195 A | 2/2007 |
| JP | 2008-296010 A | 12/2008 |
| JP | 2010-522035 A | 7/2010 |
| WO | WO 02/05721 A2 | 1/2002 |
| WO | 2008/118728 A1 | 10/2008 |

* cited by examiner

*Primary Examiner* — Darwin Erezo
*Assistant Examiner* — Katherine Schwiker
(74) *Attorney, Agent, or Firm* — Scully, Scott, Murphy & Presser, PC (57) ABSTRACT

Provided is a tissue excision method that excises a partial tissue within an excision region set in a hollow organ over an entire thickness direction. The tissue excision method includes a first process of gripping a peripheral edge portion of the excision region from the inside of the hollow organ; a second process of moving the portion and drawing the folded hollow organ into a slit with a predetermined width; a third process of suturing a part located outside the excision region so as to be integral over the thickness direction; and a fourth process of cutting the portion of the drawn hollow organ along the peripheral edge of the excision region. In the second process, a portion of a fluid within the hollow organ is moved out of the hollow organ to keep the internal pressure within a fixed range while drawing the portion of the hollow organ.

3 Claims, 8 Drawing Sheets

TISSUE EXCISION METHOD

BACKGROUND OF THE INVENTION

1. Field of the Invention

The present invention relates to a tissue excision method, and more particularly, a so-called entire-thickness excision method that excises a portion of a hollow organ over the entire thickness direction.

2. Description of Related Art

In the related art, in the medical treatment of stomach cancer or the like, excising a tumor and its surrounding tissue over the entire thickness direction of the stomach wall is performed. Such entire-thickness excision is often performed by laparotomy or laparoscopic surgery.

Additionally, a stapler for operation equipped with a pair of jaws is described in Published Japanese Translation No. 2010-522035 of the PCT International Publication.

One of the pair of jaws is mounted with a staple magazine loaded with staples, and an anvil member that has a plurality of staple pockets is attached to the other jaw. When the jaws are closed with a tissue interposed between the pair of jaws, a portion of the tissue can be cut open over the entire thickness while suturing the tissue with a staple.

SUMMARY OF THE INVENTION

The tissue excision method of the invention is a tissue excision method that excises a partial tissue within an excision region set in a hollow organ over an entire thickness direction. The tissue excision method includes a first process of gripping one point of a peripheral edge portion of the excision region from the inside of the hollow organ; a second process of moving a portion of the gripped hollow organ, folding a portion of the hollow organ so that the external surfaces of the hollow organ are in contact with each other, and drawing the folded hollow organ into a slit with a predetermined width; a third process of suturing the part located outside the excision region out of the portion of the drawn hollow organ so as to be integral over the thickness direction; and a fourth process of cutting the portion of the drawn hollow organ along the peripheral edge of the excision region. In the second process, a portion of a fluid within the hollow organ is moved out of the hollow organ to keep the internal pressure of the hollow organ within a fixed range while drawing the portion of the hollow organ into the slit.

DETAILED DESCRIPTION OF THE INVENTION

Hereinafter, an embodiment of the invention will be described with reference to FIGS. 1 to 11.

Figure 1:
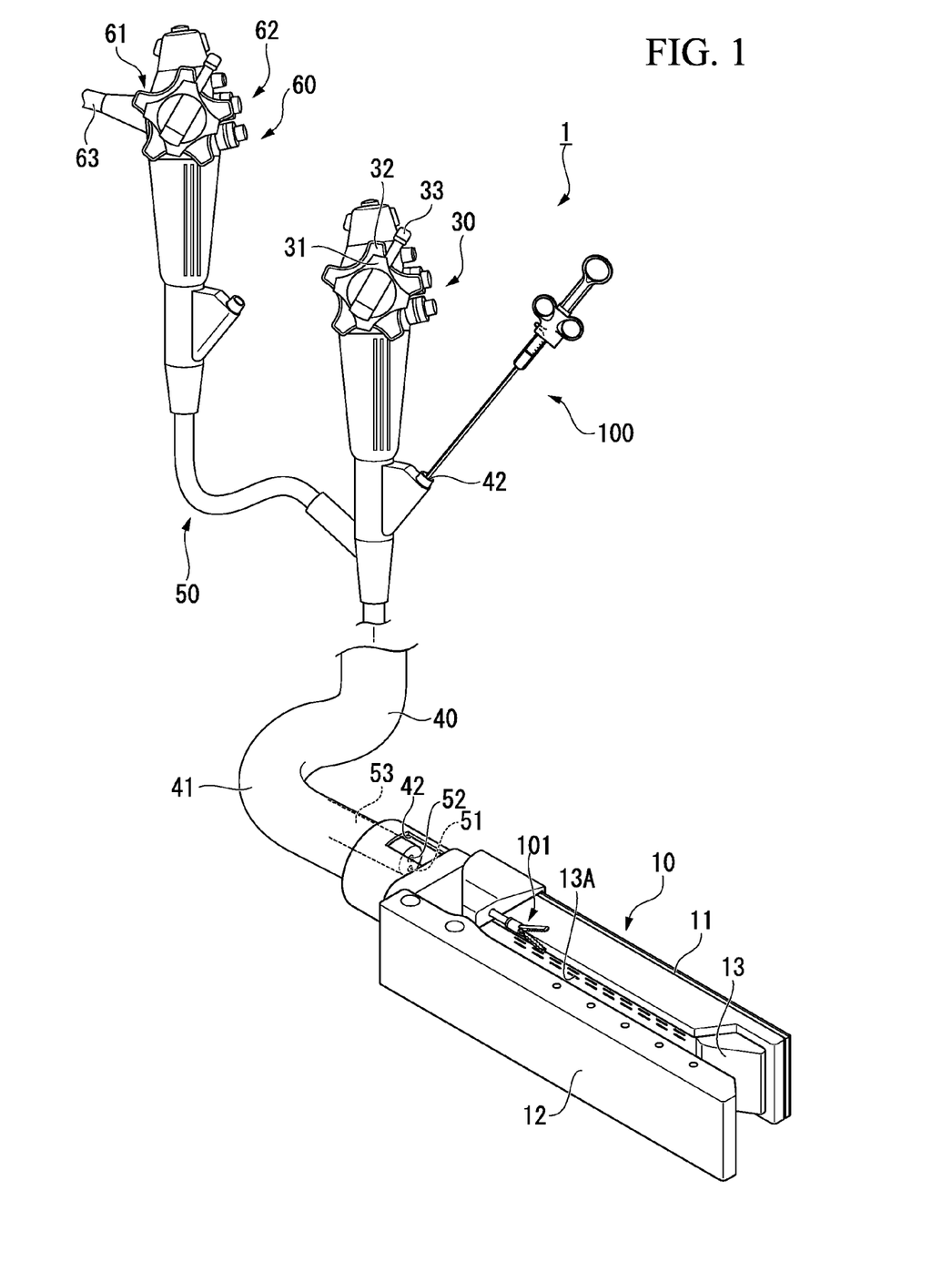
FIG. 1 is a view showing an example of a medical device favorably used for a tissue excision method of an embodiment of the invention.

As an example of a medical device favorably used for a tissue excision method of the invention, a medical device 1 equipped with a stapler is shown in FIG. 1. The medical device 1 is equipped with a treatment part 10 provided at a tip to perform a treatment on a tissue targeted, a first operating part 30 for operating the treatment part 10, an insertion part 40 provided between the treatment part 10 and the first operating part 30, an observation part 50 inserted through the insertion part 40, and a second operating part 60 for operating the observation part 50. The treatment part 10 has a first jaw (first gripping member) 11 and a second jaw (second gripping member) 12 as a pair of openable and closable jaws, and sutures and cuts off a tissue using a cartridge 13 loaded with staples 13A, and the basic structure thereof is well-known, for example, as described in the above-described Published Japanese Translation No. 2010-522035 of the PCT International Publication.

The first operating part 30 has a well-known configuration, and has two dial knobs 31 and 32 and a lever 33. The dial knob 31 is connected to the treatment part 10 by an operating member (not shown), such as a wire, and the opening and closing of the pair of jaws 11 and 12 can be operated by rotating the dial knob 31.

The insertion part 40 is formed in a tubular shape having flexibility, and has the treatment part 10 attached to the tip side thereof and the first operating part 30 attached to the base end side thereof, respectively. The insertion part 40 has a bending portion 41 of a well-known structure having a plurality of joint rings, bending frames, or the like on the tip side thereof, and can be bent by operating the dial knob 32 of the first operating part 30. The operating member is inserted through the inner cavity of the insertion part 40 so as to be able to advance and retract in its axial direction. Additionally, a forceps port 42 is provided on the base end side of the insertion part 40, and a general treatment tool 100 or the like, for an endoscope equipped with a forceps portion 101 can be inserted into the forceps port 42, and can be protruded from the base end side of the first jaw 11.

Figure 2:
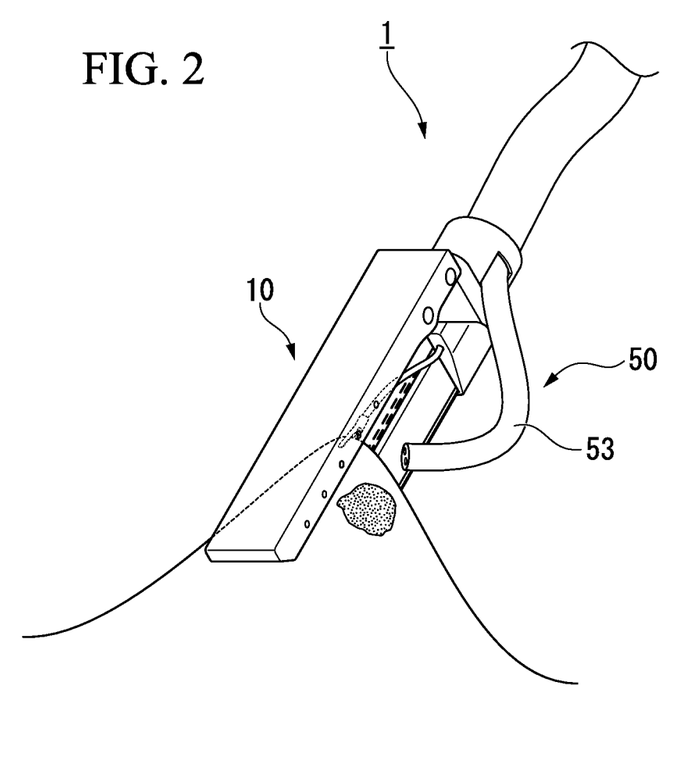
FIG. 2 is a view showing an operation when the medical device is used.

The observation part 50 is inserted through the insertion part 40 so as to be able to advance and retract, and is equipped with an illumination portion 51 including an LED or the like, or imaging portion 52, such as CCD, at the tip portion thereof. Additionally, the observation part 50 has a bending portion 53 having the same structure as the bending portion 41 on the tip side thereof. Since a tip portion of the observation part 50 can be protruded and retracted from an opening 42 provided on the tip side of the insertion part 40, the tissue held at the treatment part 10 is favorably observable by protruding the tip portion of the observation part 50, and curving the bending portion 53 appropriately, as shown in FIG. 2, for example.

The second operating part 60 is connected to a base end of the observation part 50 that comes outside from the base end side of the insertion part 40. The second operating part 60 is provided with dial knob 61, button 62, and the like, same as the first operating part 30, and the bending operation of the bending portion 53, the operation of the illumination portion 51, the imaging portion 52, and the like can be performed. A video signal acquired by the imaging portion 52 is sent to an image processing unit (not shown) through a universal cable 63, and is displayed on a display (not shown) or the like. As the observation part 50 and the second operating part 60, a well-known endoscope device or the like can be used by appropriately setting dimensions or the like.

Next, the tissue excision method of the present embodiment will be described taking a case where the entire thickness of a malignant tumor (hereinafter simply referred to as a "tumor") of the stomach (hollow organ) is excised using the medical device 1, as an example.

Figure 3:
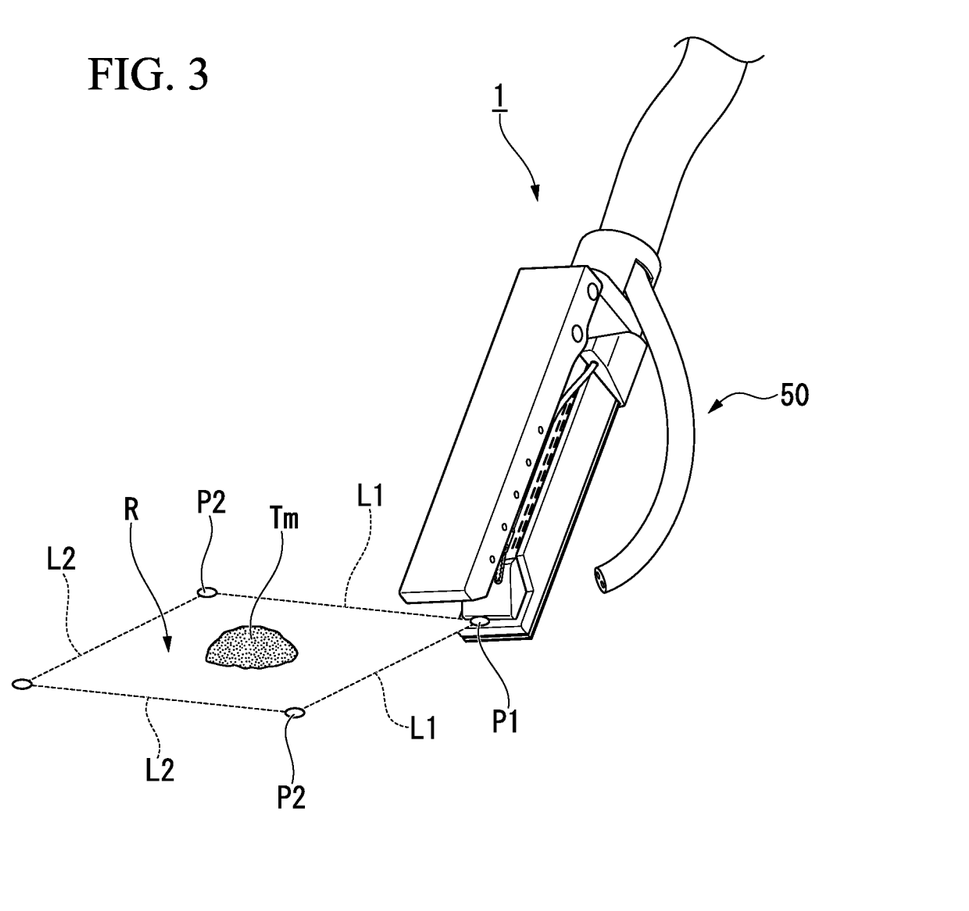
FIG. 3 is a view showing an excision region and a gripping point.

First, an operator introduces the medical device 1 into the stomach from a patient's mouth or the like, and observes a tumor using the observation part 50. Then, as shown in FIG. 3, a rough excision region R surrounding a tumor Tm is set. It is preferable that the excision region R be set so that the shortest distance from the tumor Tm becomes equal to or more than 5 mm in order not to damage the tumor Tm at the time of tissue excision.

Figure 4:
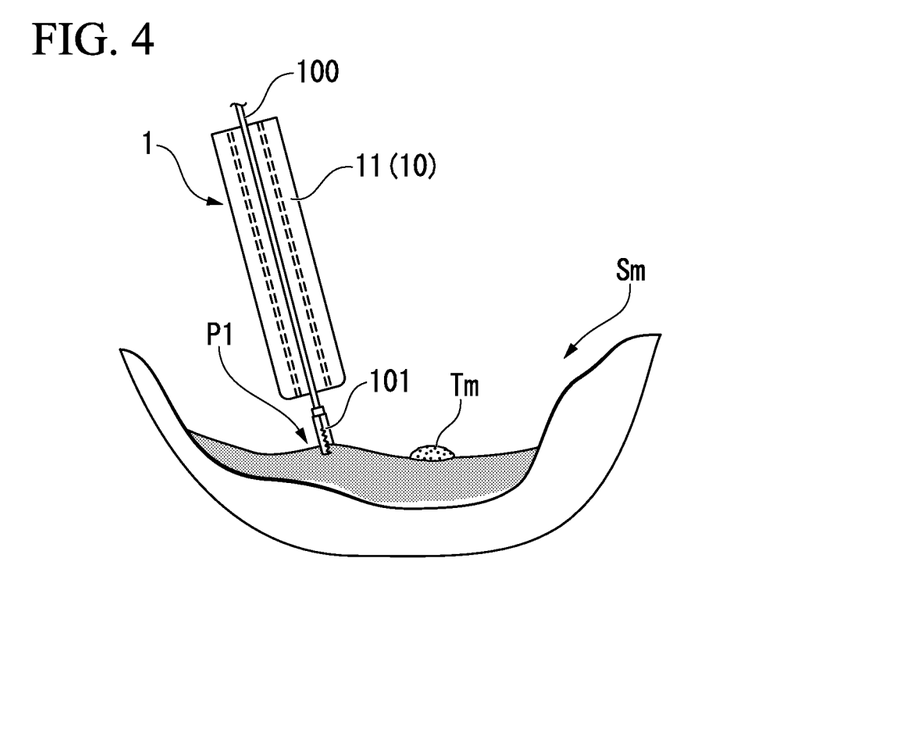
FIGS. 4 and 5 are views showing a process of this tissue excision method.

Next, the operator protrudes the treatment tool 100 from the first jaw 11, and as shown in FIG. 4, grips one point of a stomach wall away from the tumor Tm, using the forceps portion 101 from the inside of the stomach Sm (first process). Since this one point becomes a portion of the peripheral edge of a region to be actually excised, it is preferable that this point be set to a position equivalent to a peripheral edge portion of the set excision region R, for example, a part away from the center of the tumor Tm by about 30 mm can be selected. Hereinafter, this one gripping point is referred to as a first gripping point P1.

Figure 5:
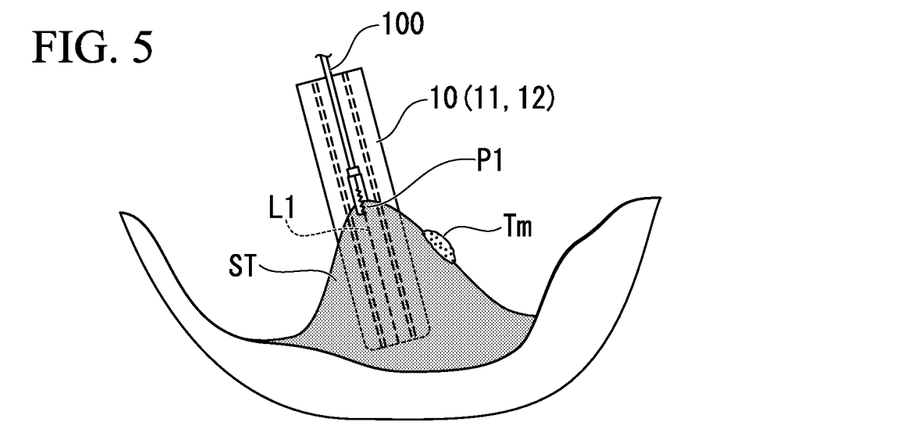

Subsequently, the operator retracts the treatment tool 100 that has gripped the first gripping point P1, and as shown in FIG. 5, draws a portion of a stomach wall tissue ST into a slit-shaped gap formed between the first jaw 11 and the second jaw 12 in a closed state (second process). The pair of jaws of the treatment part 10 may be closed in advance before gripping the first gripping point P1. Additionally, during drawing, the tumor Tm is observed by the observation part 50, and attention is paid so that the tumor Tm is not touched by the pair of jaws.

The stomach wall tissue ST is drawn between the first jaw 11 and the second jaw 12 along two first drawing lines L1 that extend from the first gripping point P1. That is, the drawn stomach wall tissue ST is folded with the external surface of the stomach being turned inward so that the external surfaces of the stomach are in contact with each other, and one drawing line of the first drawing lines L1 faces the first jaw 11 and the other drawing line L1 faces the second jaw 12. Since the gap between the pair of jaws is narrow and slit-shaped, tissues of other internal organs adjacent to the stomach are not drawn between the pair of jaws together with the stomach wall tissue.

Figure 6:
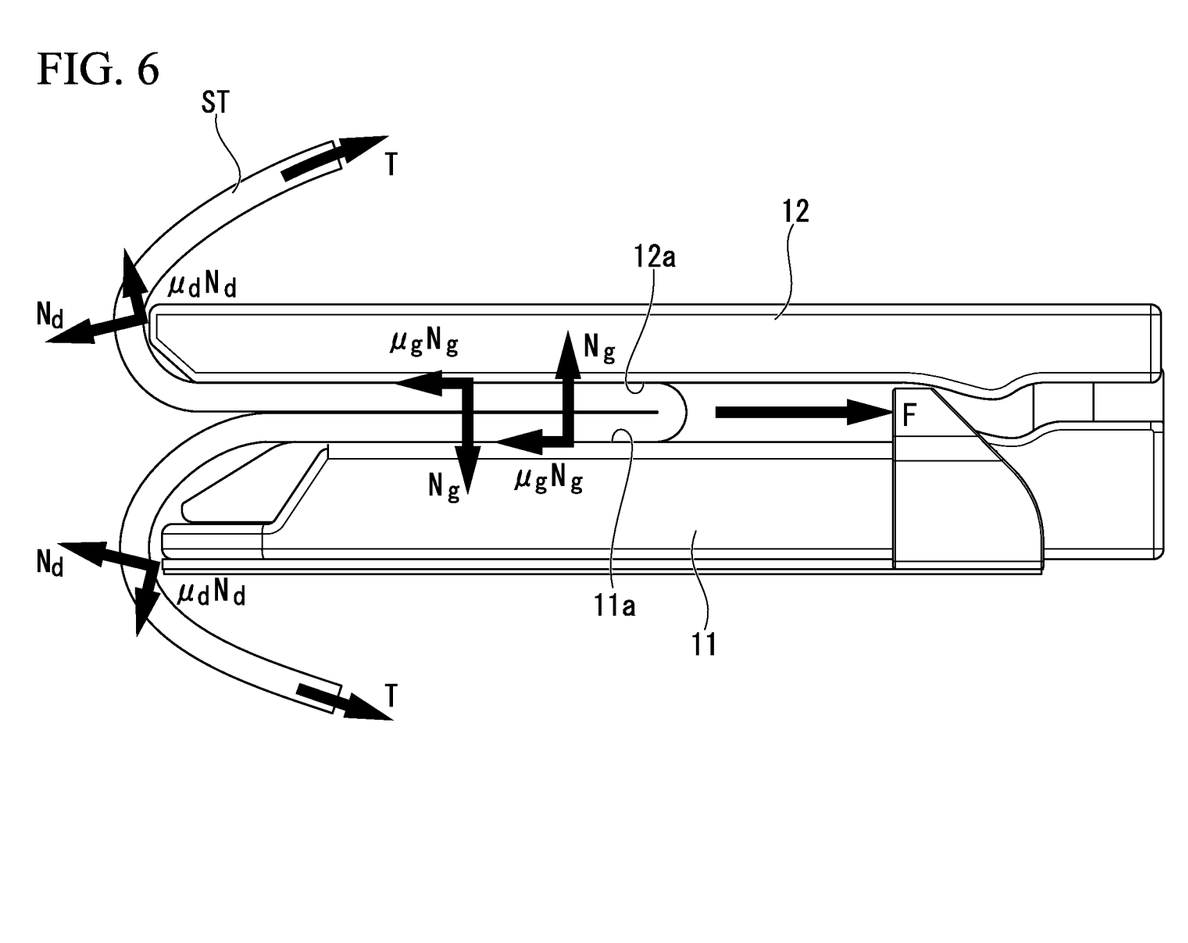
FIG. 6 is a view showing drawing force and a factor that influences the drawing force.

FIG. 6 is a view showing the drawing force required for drawing of the stomach wall tissue ST, and a factor that influences the drawing force. As for the drag when the stomach wall tissue is drawn, the tension T of the stomach wall tissue ST, the drag generated between the grip faces 11*a* and 12*a* of the pair of jaws 11 and 12 and the stomach wall, and the drag generated between tip portions of the pair of jaws and the stomach wall tissue ST are considered. Thus, if the coefficients of friction in the grip faces is $\mu_g$, the normal forces in the grip faces are $N_g$, the coefficients of friction in the tip portions are $\mu d$, and the normal forces in the tip portions are $N_d$, the stomach wall tissue ST can be drawn into the slit between the pair of jaws 11 and 12 when the following formula is established with respect to the drawing force F.

$$F \geq 2(T + \mu_g N_g + \mu d N_d)$$

Here, since the surface of the stomach wall tissue ST which comes into contact with the grip faces 11*a* and 12*a* is usually lubricous due to mucus or the like, the values of μg and μd are not so large. Accordingly, it can be said that the tension T of the stomach wall tissue ST is dominant among factors that determine the required drawing force F. Factors that determine the tension T include the elasticity of the stomach wall tissue and the internal pressure of the stomach.

Figure 7A:
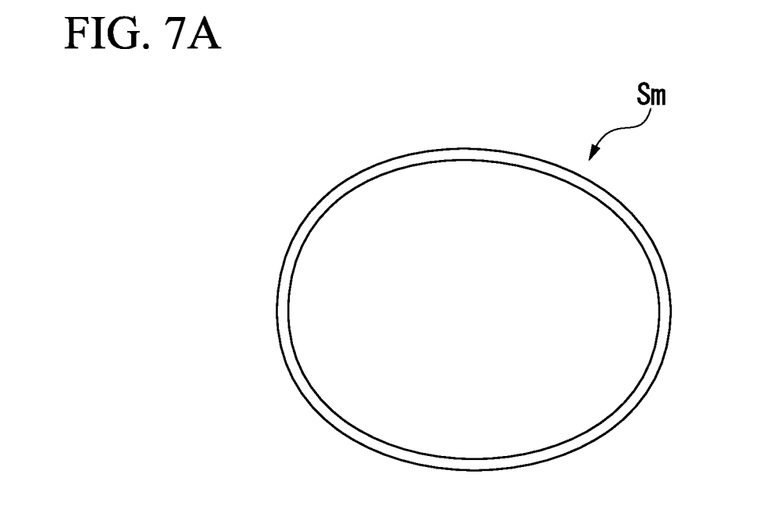
FIG. 7A is a schematic cross-sectional view of a stomach.
Figure 7B:
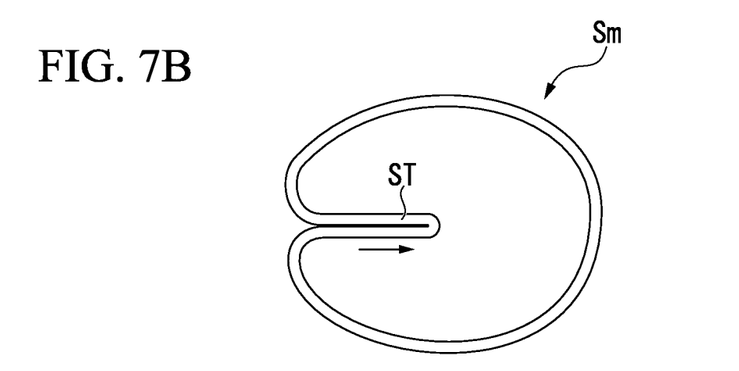
FIG. 7B is a schematic cross-sectional view when a portion of the stomach is drawn.

FIG. 7A is a schematic cross-sectional view showing the normal state of the stomach Sm, and FIG. 7B is a schematic cross-sectional view showing the state of the stomach Sm where a portion of the stomach wall tissue ST is drawn. As shown in FIG. 7B, since the stomach wall tissue ST is folded when being drawn, the volume of the stomach Sm is reduced by drawing in a portion of the stomach wall tissue ST in the second process. Accordingly, since the internal pressure of the stomach Sm rises by the drawing of the stomach wall tissue and the tension T rises if the total amount of fluids, such as air or carbon dioxide gas, does not change within the stomach, a larger drawing force F is required in order to further draw the stomach wall tissue.

Thus, in the tissue excision method of the invention, the fluid within the stomach is moved out of the stomach in parallel with the drawing of a tissue in the second process. This suppresses a rise in the tension T resulting from a rise in internal pressure, and prevents required drawing force from becoming excessively large.

Means for moving the fluid within the stomach out of the stomach is not particularly limited, and a well-known configuration can be appropriately used. For example, the observation part 50 may be provided with a suction channel, the fluid within the stomach may be suctioned from the suction channel and may be moved out of the stomach, or a suction tube may be separately introduced into the stomach to suction the fluid within the stomach.

The amount of the fluid that is moved out of the stomach is appropriately set in consideration of the internal pressure of the stomach. In the present embodiment, the internal pressure of the stomach Sm is monitored using a well-known pressure sensor or the like, and the fluid within the stomach is suctioned and discharged out of the stomach so that the value of the internal pressure is kept approximately equal to that before the drawing of the stomach wall tissue (approximately a range of ±1 to 6 mm mercury (mmHg)). This suppresses a rise in internal pressure while keeping the visual field of the observation part 50 clear during the manipulation.

Additionally, instead of the above, the reduction amount of the volume of the stomach resulting from drawing may be calculated or estimated in advance, and the movement of the fluid may be set so as to become equal to or more than the reduction amount.

Figure 8:
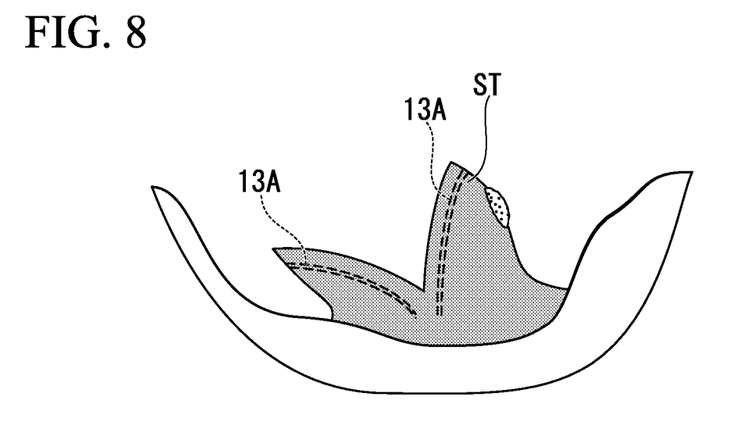
FIGS. 8 to 11 are views showing a process of this tissue excision method.

If the stomach wall tissue ST is sufficiently drawn between the pair of jaws 11 and 12, the operator operates the lever 33. Then, a wedge (not shown) bends the staples 13A within the cartridge 13 by pushing the staples toward an anvil member (not shown) provided in the second jaw 12, using a well-known mechanism. As a result, the folded stomach wall tissue ST is sutured so as to become integral along the thickness direction on both sides of the first drawing lines L1 (third process). Further, a cutter (not shown) cuts the stomach wall tissue located between the rows of the staples 13A that have sutured the stomach wall tissue ST approximately along the first drawing lines L1, and as shown in FIG. 8, a portion of the stomach wall is cut over the entire thickness (fourth process). However, since the stomach wall tissue ST is sutured with the staples 13A on both sides of a cutting line that specifies the excision region, a hole that opens to the stomach does not remain.

Figure 9:
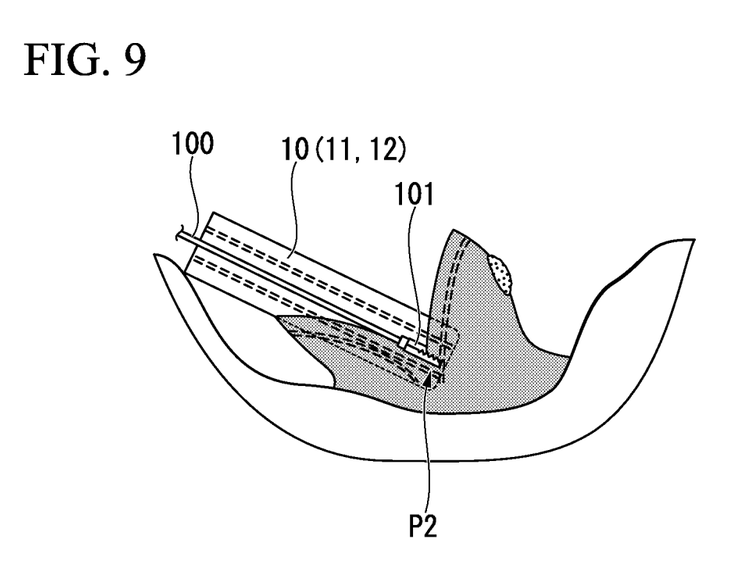

After the cutting along the first drawing lines L1 is completed, the operator extracts the medical device 1, replaces the cartridge 13, and introduces the medical device 1 into the stomach again. Then, as shown in FIG. 9, the forceps portion 101 of the treatment tool 100 grips a second gripping point P2. The second gripping point P2 is located at the end of the cutting line along the first drawing lines L1 and opposite to the first gripping point P1.

Figure 10:
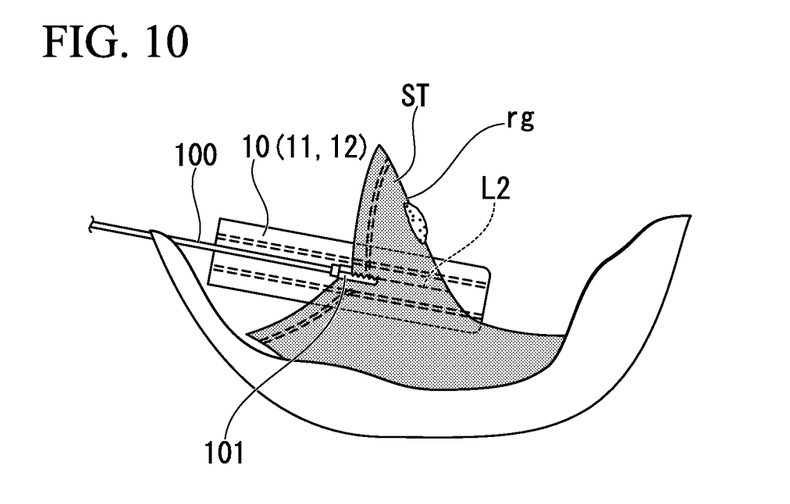

Next, the operator retracts the treatment tool 100, and as shown in FIG. 10, draws the stomach wall tissue ST gripped by the forceps portion 101 into the pair of jaws 11 and 12 along the second drawing lines L2. At this time, the stomach wall tissue ST is drawn so that a ridgeline rg of the stomach wall tissue ST that is folded so that the external surfaces of the stomach come into contact with each other passes through the inside of the pair of jaws 11 and 12.

Figure 11:
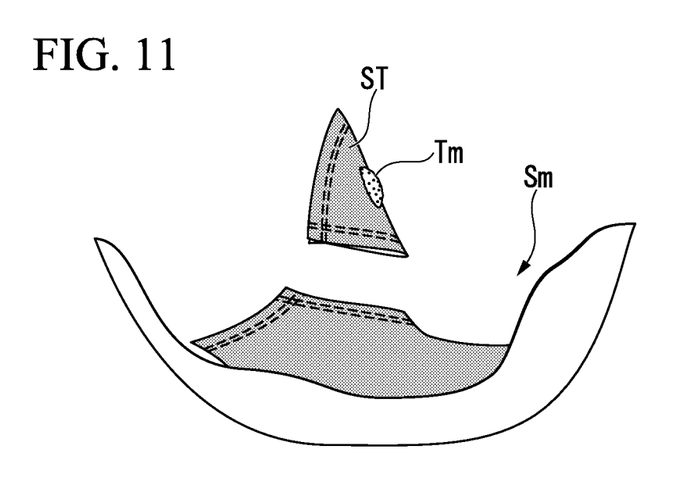

Thereafter, if suture and cutting are performed by the same operation as the above-described one, the stomach wall tissue ST is cut along the second drawing lines L2. Further, since the first drawing lines L1 and the second drawing lines L2 form a closed quadrangle as shown in FIG. 2, the stomach wall tissue ST within the excision region R including the tumor Tm is cut and separated from the stomach Sm, as shown in FIG. 11, by the cutting line formed along the first drawing lines L1 and the second drawing lines L2. In this way, a portion of the stomach wall tissue ST is excised over the entire thickness, without forming a hole that allows the stomach Sm to communicate with the abdominal cavity.

After the end of the excision, the operator extracts the medical device 1, collects the excised stomach wall tissue ST (excised piece), and ends the procedure. At this time, the excised piece is gripped by the forceps portion 101, and the extraction of medical device 1 and the collection of the excised piece may be simultaneously performed.

As described at the beginning, the entire-thickness excision in the related art has been performed through laparotomy and laparoscopic surgery. However, it has been studied that this excision is performed through natural opening such as a mouth, from the viewpoint of lessening invasiveness to the patient or of reducing the risk of recurrence when a tumor is excised.

Usually, in a case where the stomach is observed by an endoscope or the like, in order to obtain a good visual field, air is supplied to the stomach, and the stomach is inflated. Even in a case where the entire-thickness excision is performed, it is necessary to perform a procedure with sufficient observation so that a tumor is not cut. Therefore, a proper amount of gas (fluid) is needed within the stomach.

However, as shown in FIGS. 7A and 7B, if a portion of the stomach wall tissue is drawn in order to perform the entire-thickness excision, the volume of the stomach decreases. Therefore, if the amount of a fluid within the stomach is constant, the internal pressure rises. As a result, the stomach tension T increases and larger drawing force is required. Although the gripping force or drawing force of the treatment tool that grips the stomach wall tissue can be improved to some extent by the improvement of the treatment tool, there is a limit to tissue's tolerance because the thickness or the like of the tissue is usually limited to a fixed range even if individual differences are included. As a result, if the required drawing force becomes too large, the tissue cannot withstand the drawing force, and consequently, a problem may occur such that only the portion gripped by the treatment tool is torn off.

In the tissue excision method of the present embodiment, a portion of the fluid within the stomach is moved out of the stomach in the second process, whereby the internal pressure does not rise and is kept at a fixed range even if the volume of the stomach decreases due to the drawing of the tissue. Accordingly, the required drawing force does not increase excessively, and the tissue can be favorably drawn to perform entire-thickness excision.

Additionally, since the third process and the fourth process are performed after a tissue is drawn into a comparatively narrow slit-shaped gap between the pair of closed jaws 11 and 12, even if other internal organs, tissues, or the like that are adjacent to the stomach are likely to become drawn together, this is prevented by the inlet of the gap. Accordingly, even in an approach through a natural opening where the outside of the stomach cannot be visually recognized, occurrence of a situation in which these internal organs, tissues, or the likes are accidentally sutured or cut together with the stomach can be prevented.

While preferred embodiments of the invention have been described and illustrated above, it should be understood that these are exemplary of the invention and are not to be considered as limiting. Additions, omissions, substitutions, and other modifications can be made without departing from the spirit or scope of the present invention.

First, the medical device used for the tissue excision method of the invention is not limited to the one having the above-described stapler function. For example, a general curved needle, or a suture unit in which an anchor (anchors) is/are attached to one end or both ends of suture thread may be used for suturing, or so-called cold cutters, such as a scalpel, or electrical excision tools, such as an electric scalpel or a high frequency knife, may be used for cutting.

Additionally, the slit-shaped gap into which the stomach wall tissue is drawn is also not limited to the gap between the closed jaws. For example, a slit may be formed in a plate-shaped member that has fixed rigidity, and a tissue may be gripped by the grip forceps or the like to draw the tissue into the slit.

As described above, the tissue excision method of the invention can be executed if a slit holding a fixed shape even if the tissue is drawn in, means for suturing a tissue, and means for cutting the tissue are guaranteed. If the width of the slit is set to a range that is equal to or less than double the thickness of a tissue of the hollow organ, this is preferable because both drawing of the tissue and exclusion of adjacent tissues can be favorably performed.

Additionally, an example in which the pair of jaws is opened and closed by an operation has been described in the above embodiment. Instead of this, a resilient member, such as a spring, may be attached to the pair of jaws, and the pair of jaws may be always biased in the direction in which the jaws are closed by the restoring force of the resilient member. In addition, in a state where the pair of jaws is closed by the restoring force of the resilient member, a setting may be made in advance so that a slit smaller than a predetermined thickness that is drawn between the pair of jaws may be formed, or a setting may be made so that the grip faces of the pair of jaws are in contact with each other.

By adopting such a configuration, if a tissue is intended to be drawn between the pair of jaws, the pair of jaws is opened against the biasing force (restoring force) in the direction in which the jaws are closed by the resilient member, and the tissue is drawn between the pair of jaws. At this time, a folded hollow tissue is located within a slit with a predetermined width equal to the thickness of the tissue, between the pair of jaws, is brought about. As a result, similarly to the aforementioned embodiment, there is an advantage in that both the drawing of a hollow tissue and exclusion of tissues adjacent to the lumen tissue can be simultaneously performed.

Additionally, although an example in which suturing and cutting are performed twice and a tissue is excised has been described in the above embodiment, the number of times of suturing and cutting is not limited to twice. For example, in a case where a large excision region is set due to a large tumor or the like, cutting may not be made with two times depending on the size of the jaws. In such a case, if the second suturing and cutting are performed in a case where a portion of a hollow organ is drawn so that the ridgeline of the folded hollow organ does not pass through the inside of the slit, the tissue to be excised is not cut and separated after the second suturing and cutting. Thereafter, the entire thickness of a region with an arbitrary size can be excised by repeating the same suturing and cutting as needed and finally by performing suturing and cutting such that the ridgeline of the hollow organ passes through the inside of the slit.

Additionally, in the tissue excision method of the invention, the method for moving the fluid can be variously set. For example, in addition to moving the fluid in parallel with the drawing of a tissue, a predetermined amount of fluid may be moved in advance before the drawing of the tissue. However, if the fluid is excessively moved before the drawing of the tissue, there is a case where the stomach shrinks excessively and observation of a tumor or the like cannot be favorably performed. Therefore, it is preferable that the amount to be moved before the drawing of the tissue be set to a predetermined amount or less, and the stomach not to be made to shrink.

Moreover, although an example in which suturing is performed on both sides of the cutting line has been described in the above embodiment, instead of this, suturing may be performed only on one side of the cutting line that becomes the outside of the excision region. This is because the excised piece is not necessarily sutured. In this case, however, since a state where a hole temporarily opens to the hollow organ is brought about during a procedure, in a case where the hole is intended so as not to open even during the manipulation, it is preferable to perform suturing on both sides of the cutting line.

In addition, the tissue excision method of the invention is not limited to the stomach, and can be applied to other hollow organs or the like, other than the stomach. For example, although the diameter of the intestines is small compared to that of the stomach, the tissue excision method of the invention can also be favorably performed in the intestines by appropriately setting the size of devices to be used, such as a stapler.

Additionally, it is natural that the diseases whose tissues are to be excised are also not limited to the tumor described in the embodiment, and for example, can be applied to other diseases, such as a serious ulcer.

In addition, the invention is not limited by the above description and is limited only by the scope of the appended claims.

The present invention is not to be considered as being limited by the foregoing description, and is only limited by the scope of the appended claims.

What is claimed is:

1. A tissue excision method that excises a partial tissue within an excision region set in a hollow organ over an entire thickness direction, the tissue excision method comprising:
    a first process of gripping one point of a periphery of the excision region from inside of the hollow organ;
    a second process of moving a portion of the gripped excision region, folding a portion of the gripped excision region so that external surfaces of the gripped excision region are in contact with each other, and drawing the folded excision region into a slit with a predetermined width;
    a third process of fastening a part located outside of the drawn, folded excision region so as to be integral over the thickness direction; and
    a fourth process of cutting the portion of the drawn, folded excision region along the periphery of the excision region,
    wherein in the second process, a portion of a fluid within the hollow organ is moved out of the hollow organ to keep the internal pressure of the hollow organ within a fixed range while drawing the folded excision region into the slit.

2. The tissue excision method according to claim 1,
    wherein in the third process, a part located inside the excision region in addition to a part located outside the excision region is fastened so as to be integral over the thickness direction, and
    in the fourth process, the part located outside the excision region and the part located inside the excision region are cut therebetween.

3. The tissue excision method according to claim 1, wherein in the second process, the fluid moved out of the hollow organ is an amount equal to or more than a volume of the hollow organ that is decreased as the folded excision region is drawn into the slit.

* * * * *